United States Patent
Pemberton et al.

(10) Patent No.: US 9,499,575 B2
(45) Date of Patent: Nov. 22, 2016

(54) SYNTHESIS OF CARBOHYDRATE-BASED SURFACTANTS

(71) Applicant: THE ARIZONA BOARD OF REGENTS ON BEHALF OF THE UNIVERSITY OF ARIZONA, Tucson, AZ (US)

(72) Inventors: Jeanne E. Pemberton, Tucson, AZ (US); Robin L. Polt, Tucson, AZ (US); Raina M. Maier, Tucson, AZ (US); Clifford S. Coss, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 112 days.

(21) Appl. No.: 14/041,251

(22) Filed: Sep. 30, 2013

(65) Prior Publication Data

US 2014/0142287 A1    May 22, 2014

Related U.S. Application Data

(60) Provisional application No. 61/796,653, filed on Nov. 16, 2012.

(51) Int. Cl.
| | |
|---|---|
| *C07H 9/04* | (2006.01) |
| *C07H 13/04* | (2006.01) |
| *C07H 15/04* | (2006.01) |
| *C07H 15/06* | (2006.01) |
| *C07H 1/00* | (2006.01) |
| *C07F 9/94* | (2006.01) |
| *C07H 15/14* | (2006.01) |
| *C07F 3/00* | (2006.01) |

(52) U.S. Cl.
CPC ............... *C07H 15/06* (2013.01); *C07F 3/003* (2013.01); *C07F 9/94* (2013.01); *C07H 1/00* (2013.01); *C07H 15/04* (2013.01); *C07H 15/14* (2013.01)

(58) Field of Classification Search
None
See application file for complete search history.

(56) References Cited

U.S. PATENT DOCUMENTS 5,166,337 A * 11/1992 Ripke ................... C07H 15/04
536/120

OTHER PUBLICATIONS

Ikeda et al., Bioorganic and Medicinal Chemistry, vol. 11(14), Jul. 2003, pp. 3073-3076.*
Cross, C.S., Minimally Competent Lewis Acid Catalysts. General Methods for the Synthesis and Separation of Diastereomeric Mixtures of Monorhamnolipids of Pseudomonas aeruginosa with Peracetate Glycoside Donors, Ph.D. dissertation, 2012, 1-274, University of Arizona.
Cross, C.; Carrocci, T.; Maier, R.M.; Pemberton, J.E.; and Polt, R., . Minimally Competent Lewis Acid Catalysts: Indium(III) and Bismuth(III) Salts Produce Rhamnosides (=6-Deoxymannosides) in High Yield and Purity, Helvetica Chimica Acta, 2012, 2652-2659, vol. 95.
Zhang, L.; Veres-Schalnat, T.A.; Somogyi, A.; Pemberton, J.E.; Maier, R.M., Fatty Acid Cosubstrate (β-Oxidation Provides Precursors for Rhamnolipid Biosynthesis in Pseudomonas aeruginosa: Evidence from Isotope Tracing and Gene Expression, Applied and Environmental Microbiology, 2012, 8611-8622, vol. 78.
Ahad, S.M.; Ange, Al.; Ates, R.B.; Bell, B.L.; Bodour, A.A.; Bourne, B.R.; Conteras, C.G.; Goldberg, E.L.; Gunatilaka, A.A.L.; King, S.; Lee, A.K.; Low, R.L.; Maier, R.M.; Marlor, K.M.; Marron, M.T.; Scolnik, R.C.; Streeter, M.J.; Strelczuk, M.; Trinh, L.N.; Truong, V.K.; Vissering, S.P.; Weick, M.C.; Williams, M.T., Synthesis and Biological Activities of Flavolipids, Tetrahedron, 2010, 9107-9112, vol. 66.
Sani, H.S.; Barragán-Huerta, B.E.; Lebrón-Paler, A.; Pemberton, J.E.; Vásquez, R.R.; Burns, A.M.; Marron, M.T.; Seliga, C.J.; Gunatilaka, A.A.L.; Maier, R.M., Efficient Purification of the Biosurfactant Viscosin from Pseudomonas libanensis Strain M9-3, and Its Physicochemical and Biological Properties, J. Nat. Prod., 2008, 1011-1015, vol. 71.
Neilson, J.W.; Zhang, L.; Veres-Schalnat, T.A.; Chandler, K.B.; Neilson, C.H.; Crispin, J.D.; Pemberton, J.E.; Maier, R.M., Cadmium Effects on Transcriptional Expression of rhlB/rhlC Genes and Congener Distribution of Monorhamnolipid and Dirhamnolipid in Pseudomonas aeruginosa IGB83, Appl. Microbiol. Biotechnol., 2010, 953-963, vol. 88.
Lebrón-Paler, A.; Pemberton, J.E.; Otto, W.C.; Becker, B.K.; Larive, C.K.; Maier, R.M., Determination of the Acid Dissociation Constant of the Biosurfactants Monorhamnolipid in Aqueous Solution by Potentiometric and Spectroscopic Methods, Anal. Chem., 2006, 7649-7658, vol. 78.
Lebrón-Paler, A., Solution and Interfacial Characterization of Rhamnolipid Biosurfactant from P. aeruginosa ATCC 9027, Ph.D. dissertation, 2008, 1-481, University of Arizona.
Kitamoto, D.; Hisoda, H.; Nakahara, T.J., Functions and Potential Applications of Glycolipid Biosurfactants, from Energy Saving-Materials to Gene Delivery Carriers, Journal of Bioscience and Bioengineering, 2002, 187-201, vol. 94.
Al-Tahhan, R.A.; Sandrin, T.R.; Bodour, A.A.; Maier, R.M., Rhamnolipid-Induced Removal of Lipopolysaccharide from Pseudomonas aeruginosa: Effect of Cell Surface Properties and Interaction with Hydrophobic Substrates, Applied and Environmental Microbiology, 2000, 3262-3268, vol. 66.
Bauer, J.; Brandenburg, K.; Zähringer, U.; Rademann, J., Chemical Synthesis of a Glycolipid Library by a Solid-Phase Strategy Allows Elucidation of the Structural Specificity of Imnnunistimulation by Rhamnolipids, Chemistry, a European Journal, 2006, 7116-7124, vol. 12.
Wakao, M.; Suda, Y., Synthesis of Glycolipids, Glycoscience, 2008, 1629-1669, Kagoshima, Japan.
Schmidt, R.R., New Methods for the Synthesis of Glycosides and Oligosaccharides—Are There Alternatives to the Koenigs-Knorr Method?, Angew. Chem. Int. Ed. Engl., 1986, 212-235, vol. 25.

(Continued)

*Primary Examiner* — Traviss C McIntosh, III
(74) *Attorney, Agent, or Firm* — Don D. Cha; Hamilton DeSanctis & Cha, LLP

(57) ABSTRACT

The present invention provides carbohydrate-based surfactants and methods for producing the same. Methods for producing carbohydrate-based surfactants include using a glycosylation promoter to link a carbohydrate or its derivative to a hydrophobic compound.

11 Claims, No Drawings

(56) References Cited

OTHER PUBLICATIONS

Lefever, M.R.; Szabó, L.; Anglin, B.; Ferracane, M.; Hogan, J.; Cooney, L.; Polt, R., Glycosylation of α-Amino Acids by Sugar Acetate Donors with InBr3. Minimally Competent Lewis Acids, Carbohydrate Research, 2012, 121-125, vol. 351.

Lindhost, T.K.; Essentials of Carbohydrate Chemistry and Biochemistry, 6 Structure and Biosynthesis of Glycoconjugates, 2007, 224-225, 2nd Ed., New York.

Witczak, Z.J., Current Medicinal Chemistry, Thio Sugars: Biological Relevance as Potential New Therapeutics, 1999, 165-178, vol. 6.

Dalhoff, W.V., Synthesis of a Series of Alkyl 1-Thio-D-Glucopyranosides and Their Regioselective Reductions to 1-Alkylthio-1-Deoxy-D-Glucitols, Liebigs Ann. Chem., 1990, 1025-1027.

Nakajima, H.; Miura, Y.; Yamagata, T.J., Glycosylation of Amphipathic Lactoside Primers with Consequent Inhibition of Endogenous Glycosphingolipid Synthesis, J. Biochem., 1998, 148-156, vol. 124.

Leonard, N.M.; Weiland, L.C.; Mohan, R.S., Applications of Bismuth (III) Compounds in Organic Synthesis, Tetrahedron, 2002, 8373-8397, vol. 58.

Ikeda, K.; Torisawa, Y.; Nishi, T.; Minamikawa, J.; Tanaka, K.; Sato, M., Glycosylation of Sialyl Acetates with a Novel Catalyst Combination:Bismuth Triflate and BF3.OET2 System, Bioorganic & Medicinal Chemistry, 2003, 3073-3076, vol. 11.

Watanabe, Y.; Nakamosto, C.; Ozaki, S., Glycosylation Based on Phosphite Chemistry, Synlett, 1993, 115-116.

Wang, H.; Solution and Interfacial Characterization of Rhamnolipid Biosurfactants and their Synthetic Analogues, Ph. D. dissertation, 1-368, University of Arizona.

Wang, H.; Coss, C.S.; Mudalige, A.; Polt, R.L.; Pemberton, J.E., A PM-IRRAS Investigation of Monorhamnolipid Orientation at the Air-Water Interface, Langmuir, 2013, 4441-4450, vol. 29.

Kiyoshi Ikeda et al., "Glycosylation of Sialyl Acetates with a Novel Catalyst Combination: Bismuth Triflate and BF3 OEt2 System", 2003, Bioorganic & Medicinal Chemistry 11, pp. 3073-3076.

J. Lokesh Babu; Anakshi Khare; and Yashwant D. Vankar, "Bi(OTf)3 and Sio2-Bi(OTf)3 as Effective catalysts for the Ferrier Rearrangement#", 2005, Molecules, pp. 884-892.

Takashi Yamanoi; Ryo Inoue; Sho Matsuda; and Keita Hamasaki, "Bismuth(III) Triflated-Catalyzed Dehydrative Glycosidation Using 1-Hydroxy Sugars", 2008, Letters in Organic Chemistry, vol. 5, pp. 30-33.

Clifford Coss et al., "Minimally Competent Lewis Acid Catalysts: Indium(III) and Bismuth(III) Salts Produce Rhamnosides (=6-Deoxymannosides) in High Yield and Purity", 2012. Helvetica Chimica Acta, vol. 95, pp. 2652-2659.

\* cited by examiner

SYNTHESIS OF CARBOHYDRATE-BASED SURFACTANTS

CROSS-REFERENCE TO RELATED APPLICATIONS

This application claims the priority benefit of U.S. Provisional Application No. 61/796,653, filed Nov. 16, 2012, which is incorporated herein by reference in its entirety.

STATEMENT REGARDING FEDERALLY FUNDED RESEARCH

This invention was made with government support under Grant Nos. CHE0714245 and CHE0133237 awarded by the National Science Foundation, Grant No. P42 ES004940 awarded by the National Institutes of Health, and Grant No. DE-FG03-93ER61526 awarded by the Department of Energy. The government has certain rights in the invention.

FIELD OF THE INVENTION

The present invention relates to novel surfactants and methods for producing the same. In particular, surfactants of the invention comprise a carbohydrate-based hydrophilic group and a lipid or a hydrocarbon hydrophobic group. Methods for producing carbohydrate-based surfactants include using a glycosylation promoter to link a carbohydrate compound or its derivative to a hydrophobic compound.

BACKGROUND OF THE INVENTION

Today's market for amphiphilic molecules, including surfactants, emulsifiers, wetting control agents, drug and gene delivery agents, microencapsulents, nanoparticle growth agents, cleaning products, and food and cosmetic additives, is mostly comprised of synthetic surfactants prepared from petroleum-based starting materials. Not only have many synthetic amphiphiles shown acute toxicities in water supplies and soil after being deposited, but they also are dependent on nonrenewable and increasingly costly petroleum. The solution to this ongoing problem is the synthesis (biological and/or chemical) of naturally-occurring (e.g. biosurfactants) or new, biodegradable amphiphilic glycolipids. Although many amphiphilic glycolipids are used in industry, they are difficult to produce on a large scale and purity is often low. A low-cost synthesis of glycolipid amphiphiles is a requirement in a market that includes many oils and synthetic amphiphiles that can be produced at pennies per pound.

As one example of biosurfactants, rhamnolipids consist of one or more rhamnose (i.e., 6-deoxy-α-L-mannose) moieties and an ester-linked di-lipid tail. They have been found in the Gram-negative bacteria such as *Acinetobacter calcoaceticus, Enterobacter asburiae, Enterobacter hormaechei, Pantoea stewartii*, and *Pseudomonas aeruginosa*. Biosynthetic production of rhamnolipids via the mutant strain of bacteria, *P. aeruginosa* ATCC 9027 (a mutant that produces specifically monorhamnolipids) produces about 40 different monorhamnolipid congeners with a variety of saturated and unsaturated lipid chain lengths (ranging from $C_6$ to $C_{18}$); the fully-saturated $C_{10}$,$C_{10}$ monorhamnolipid being the most dominant (~80% of mixture). Rhamnolipids, and many known amphiphilic glycolipids, are good foaming and wetting agents and are able to increase aqueous solubility of hydrophobic compounds, making them excellent solubilizing and emulsifying agents for diverse applications. In food, rhamnolipids are used as emulsifiers (e.g., partial broken fat tissue) and for influencing the rheological properties of flour. In agriculture, they are used for dilution and dispersion of fertilizers and pesticides in order to increase product penetration into plants. In cosmetics, they are used as soaps and soap formulators. In industry, they are used for emulsion polymerization of paints and industrial coatings. In the pharmaceutical industry, they are used to influence hydrophobicity of Gram-negative cell walls, allowing for easier attack by hydrophobic antibiotics. Furthermore, rhamnolipids have been shown to be environmentally friendly, expressing low toxicity and biodegradable characteristics, as well as showing strong evidence for bioremediation of hydrocarbons, organic pollutants (including green-house gases), and heavy-metal contamination.

Many amphiphiles are naturally-occurring materials that are biosynthesized and extracted from animals, plants and bacteria. However, these compounds are difficult to biosynthesize on a large scale, and purification can be difficult to impossible if a complex mixture of congeners is produced. Based on their putative biodegradability and low toxicity, biosurfactants and other amphiphilic glycolipids have great potential as "green" alternatives to the sometimes carcinogenic and toxic synthetic amphiphiles in the market. More specifically, large-scale production of the glycolipid class of biosurfactants is of great interest because of their excellent surfactant characteristics, their demonstrated use in bioremediation; the existence of evidence supporting their susceptibility to biodegradation, and their applications from paper, plastics, cosmetics, foods, pesticides, medicine, etc.

While there is a high demand for these carbohydrate or a derivative-based surfactants, conventional methods for producing such surfactants require utilizing bacteria or other microorganisms, which significantly increases their production and purification costs. In addition, microorganism based biosurfactant production limits the number of biosurfactants that can be produced and, therefore, surfactant's properties cannot be readily tailored. Many chemical processes for producing biosurfactants often utilize a toxic material or are low yielding, thereby rendering many such processes not commercially viable.

Therefore, there is a need for a cost-effective and environmentally friendly method for producing biosurfactants such as carbohydrate- or its derivative-based surfactants.

SUMMARY OF THE INVENTION

Syntheses of glycolipids typically involve expensive and toxic reagents, dangerous procedures, and low yielding reactions. Methods of the invention minimize or eliminate these problems and limitations. In one particular embodiment, methods of the invention include a cost-effective glycosylation reaction that utilizes a glycosylation promoter. The generality of the methods of the invention allows for synthesis of a broad array of carbohydrate-based surfactants such as glycolipids. Moreover, methods of the invention minimize the number of reaction steps, cost, and time compared to conventional glycolipid syntheses.

One particular aspect of the invention provides a method for producing a surfactant, said method comprising contacting a hydrophilic compound with a hydrophobic compound in the presence of a catalytic amount of a bismuth-based promoter under conditions sufficient to form a covalent bond between said hydrophilic compound and said hydrophobic compound to produce a surfactant, wherein said hydrophobic compound comprises a functional group selected from the group consisting of an amine group, a hydroxyl group and a thiol group. The heteroatom (e.g., O, N, or S) of the functional group of said hydrophobic compound becomes attached to the hydrophilic compound.

In one embodiment, said bismuth-based promoter comprises bismuth trifluoromethanesulfonate, bismuth halide, or a mixture thereof.

Yet in other embodiments, the amount of bismuth-based promoter is about 0.25 equivalent or less.

Still in other embodiments, the amount of bismuth-based promoter is about 0.1 equivalent or less.

In other embodiments, said hydrophilic compound is a carbohydrate or a derivative thereof. Within these embodiments, in some instances said carbohydrate comprises a hydroxy protecting group. Suitable hydroxy protecting groups for methods of the invention include, but are not limited to, are esters such as acetyl, benzoyl, trifluoroacetyl, propanoyl, formyl, etc.

Yet in other embodiments, said hydrophobic compound is a hydrocarbon compound of the formula: $R^x$—X, where Rx is hydrocarbon and X is —OH, —NH$_2$ or —SH. In some instances, $R^x$ is alkyl. Still in other instances X is —OH or —SH. Yet in other instances X is —OH.

In some embodiments, said hydrophobic compound comprises (e.g., $R^x$ is) a $C_6$-$C_{30}$ alkyl chain. Typically, said hydrophobic compound comprises a $C_6$-$C_{18}$ alkyl chain.

Another aspect of the invention provides a method for producing a glycolipid, said method comprising contacting a carbohydrate with a lipid in the presence of a catalytic amount of a bismuth-based glycosylation promoter under conditions sufficient to produce a glycolipid, wherein said lipid comprises a glycosylation functional group selected from the group consisting of an amine group, a hydroxyl group and a thiol group, and wherein said lipid is glycosylated at said glycosylation functional group.

Yet other aspects of the invention provide a method for producing a carbohydrate- or its derivative-based surfactant, said method comprising contacting a carbohydrate or its derivative with a hydrophobic compound in the presence of a catalytic amount of a glycosylation promoter under conditions sufficient to form a covalent bond between said carbohydrate or its derivative and said hydrophobic compound to produce a carbohydrate- or its derivative based surfactant, wherein said hydrophobic compound comprises a functional group selected from the group consisting of an amine group, a hydroxyl group and a thiol group, and wherein the functional group of said hydrophobic compound covalently links said hydrophobic compound to said carbohydrate or its derivative.

In some embodiments, said glycosylation promoter comprises a bismuth (III) compound, a scandium (III) compound, a boron compound, an indium (III) compound or a mixture thereof. Yet in other embodiments, said glycosylation promoter comprises a bismuth (III) compound. Within these embodiments, in some instances said bismuth (III) compound comprises bismuth trifluoromethanesulfonate, bismuth halide, or a mixture thereof.

Yet in other embodiments, the amount of glycosylation promoter used in the reaction is about 0.25 equivalent or less. It should be appreciated that the term "equivalent" is relative to the amount of either the hydrophilic or the hydrophobic compound used in the reaction, whichever is less.

Still in some embodiments, said hydrophobic compound is a hydrocarbon compound of the formula: $R^x$—X, where Rx and X are those defined herein.

In other embodiments, said hydrophobic compound comprises a $C_6$-$C_{30}$ alkyl chain. Within these embodiments, in some instances said hydrophobic compound comprises a $C_6$-$C_{18}$ alkyl chain.

Still other aspects of the invention provides a carbohydrate- or its derivative-based surfactant of the formula:

A-B wherein

A is selected from the group consisting of:

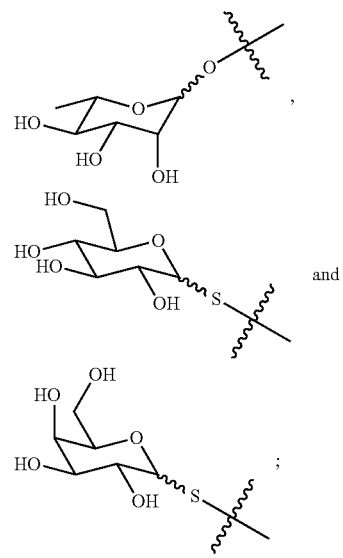

and

B is selected from the group consisting of:

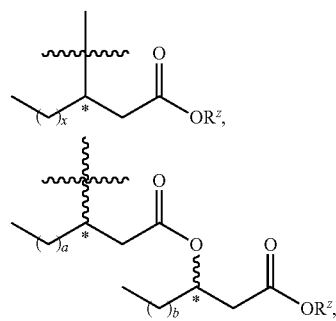

or $C_6$-$C_{30}$ hydrocarbon;

and wherein $R^z$ is hydrogen, alkyl, benzyl, or other carboxylic acid protecting group;

x is an integer from 6 to 14;

a is an integer from 2 to 18;

b is an integer from 2 to 18; and

* is a chiral center.

In some embodiments, $C_6$-$C_{30}$ hydrocarbon is $C_6$-$C_{30}$ alkyl.

In one particular embodiment, A is

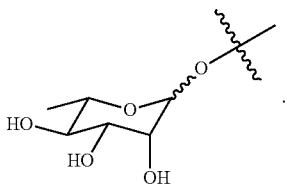 [SMILES: *OC1OC(C)C(O)C(O)C1O]

In some instances within this embodiment, B is

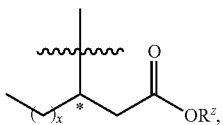

wherein $R^z$, x and * are those defined herein. In some cases, x is 6, 10, 12 or 14. Still in other instances, B is

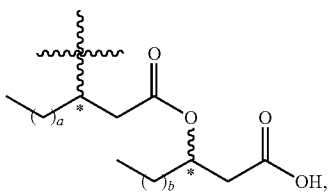

wherein a, b and * are those defined herein. In some cases, a is 2, 6, 10, 12 or 14. In other cases, b is 2, 4, 6, 8, 10, 12 or 14. Yet in other instances, B is $C_9$ or $C_{10}$ alkyl. In some cases, B is a straight chain $C_9$ or $C_{10}$ alkyl. Typically, 1- or 2-position of $C_9$ or $C_{10}$ alkyl is linked to A.

Still in another embodiment, A is

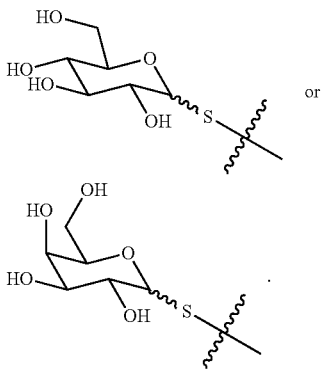

In some instances, B is $C_6$-$C_{30}$ alkyl. In one particular case, B is dodecyl.

DETAILED DESCRIPTION OF THE INVENTION

Definitions

When referring to a nonpolar or hydrophobic alkyl group, the term "alkyl" refers to a monovalent saturated linear monovalent hydrocarbon moiety or a saturated branched monovalent hydrocarbon moiety of six to thirty, typically six to twenty two, often six to twenty and more often six to eighteen carbon atoms. Exemplary nonpolar alkyl groups include, but are not limited to, hexyl, decyl, dodecyl, tetradecyl, hexadecyl, octadecyl, and the like.

A nonpolar or hydrophobic "alkenyl" group refers to a linear monovalent hydrocarbon moiety or a branched monovalent hydrocarbon moiety having at least one carbon-carbon double bond in which the total carbon atoms is six to thirty, typically six to twenty two, often six to twenty and more often six to eighteen. Exemplary nonpolar alkenyl groups include, but are not limited to, hexyl, decyl, dodecyl, hexadeca-1,3-dienyl, docosahexaenyl, dodeca-2,4-dienyl, and the like.

A nonpolar or hydrophobic "alkynyl" group refers to a linear monovalent hydrocarbon moiety or a branched monovalent hydrocarbon moiety having at least one carbon-carbon triple bond in which the total carbon atoms is six to thirty, typically six to twenty two, often six to twenty and more often six to eighteen. Alkynyl group can optionally have one or more alkenyl moiety (i.e., carbon-carbon double bond). Exemplary nonpolar alkynyl groups include, but are not limited to, hexynyl, decynyl, dodecynyl, hexadeca-1,3-diynyl, dodecynyl, dec-1-en-3-ynyl and the like.

The terms "halo," "halogen" and "halide" are used interchangeably herein and refer to fluoro, chloro, bromo, or iodo.

The term "hydrocarbon" includes alkyl, alkenyl, or alkynyl as defined herein. It should be appreciated that one or more of the hydrogen in alkyl, alkenyl, or alkynyl may be substituted with halide. Unless stated otherwise, hydrocarbon can also include a cyclic (alkyl, alkenyl or alkynyl) group or an aryl group, provided that the overall polarity of the hydrocarbon remains relatively nonpolar.

The term "hydrophobic" group refers to any moiety having at least six carbon atoms in which in the absence of the hydrophilic portion of the surfactant is substantially immiscible or insoluble in aqueous solution. Typically, solubility of the parent hydrophobic group (i.e., where the hydrophilic portion of the surfactant is replaced with hydrogen or the corresponding functional group) in water is about 10 g/L or less, often 1 g/L or less, more often 0.5 g/L or less, and most often 0.1 g/L or less. The hydrophobic group can have other functional groups (e.g., ether, ester, halide, etc.) as long as the solubility of the parent compound satisfies the conditions set forth herein. Thus, the term hydrophobic group includes hydrocarbons defined herein as well as lipids, and other groups in which the parent compound meets the conditions set forth herein.

"Aryl" refers to a monovalent mono-, bi- or tricyclic aromatic hydrocarbon moiety of 6 to 15 ring carbon atoms which is optionally substituted with one or more, typically one, two, or three substituents within the ring structure. When two or more substituents are present in an aryl group, each substituent is independently selected. Typical substituents for an aryl group include, but are not limited to, alkyl, alkenyl, alkynyl, and halide.

The term "derivative" refers to any chemical modification of the parent compound or a compound derived from the parent compound. For example, a derivative of a carbohydrate includes alkylated carbohydrate, replacement of one or more hydroxyl groups with hydrogen, halide, amine, or a thiol; modification of a hydroxyl group (e.g., by esterification, etherification, protection, etc.); as well as other derivatives known to one skilled in the art. The term carbohydrate includes pyranose and furanose carbohydrates. Exemplary derivatives of carbohydrates include, but are not limited to, alkylated carbohydrate (e.g., one or more hydroxyl groups that are methylated, ethylated, acetylated, or benzoylated), thiol carbohydrate (where one or more hydroxyl groups are replaced with —SH moiety), deoxy carbohydrates (where one or more —OH groups of the carbohydrate is replaced with —H), etc.

Unless the context requires otherwise, the term "promoter" refers to a compound that facilitates or aids in linking a hydrophilic compound with a hydrophobic compound to produce a surfactant. The promoter itself does not become part of the final product (i.e., surfactant) but merely facilitates formation of a bond between the hydrophilic group and the hydrophobic group. A promoter can be a catalyst, in which case less than 1 equivalent can be used, or it can be stoichiometric, requiring at least 1 equivalent.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Surfactants

Surfactants are compounds that lower the surface tension (or interfacial tension) between two liquids or between a liquid and a solid. Typically, surfactants are amphiphilic organic compounds that can form aggregates in solution and ordered assemblies at interfaces. Surfactants can act as detergents, wetting agents, emulsifiers, foaming agents, and dispersants. Surfactants typically include two different groups, a hydrophilic or polar group and a hydrophobic or a nonpolar group. Typical hydrophobic groups of a surfactant are a lipid or other nonpolar hydrocarbon group such as an alkyl, alkenyl, or alkynyl. However, it should be appreciated that suitable nonpolar groups for a surfactant are not limited to these groups and can include any nonpolar groups including cyclic hydrocarbon group, aromatic hydrocarbon group, etc.

When placed in an aqueous solution, surfactants form a micelle where the lipophilic tails of the surfactant remain on the inside of the micelle due to its hydrophobicity. The polar "heads" of the micelle, due to its hydrophilic property, form a hydrophilic outer layer that in effect protects the hydrophobic core of the micelle. It should be noted that surfactants are soluble not only in polar protic solvents such as water but also in polar aprotic and non-polar solvents as a reverse micelle.

Thus surfactants are useful in a wide variety of applications including, but not limited to, household detergents, industrial and institutional cleaning, personal care products, crop protection, agricultural dispersants, oil drilling and extraction, paints and coatings, textile spin finishes, textile auxiliaries, construction, emulsion polymerization, food additives, leather production, mining, plastics additives, pulp and paper, explosives, remediation, wetting control agents, pharmaceuticals, drug delivery agents, etc.

Unfortunately, conventional surfactant syntheses are typically toxic or have a high environmental impact in that toxic chemicals do not degrade readily and can last for years. Current "green" alternatives for surfactants include biosurfactants and other naturally-occurring and/or bio-inspired surfactants. However, these green surfactants are typically limited to known biosurfactants and, therefore, surfactant's properties cannot be readily tailored.

Some aspects of the invention are directed to surfactants that are biodegradable and have generally low toxicity. Other aspects of the invention provide methods for producing the same. In particular, surfactants of the invention are of the formula:

$$R^1-(X-R^2)n$$

where $R^1$ is a hydrophilic group, $R^2$ is a hydrophobic group, each X is independently a functional group that links the hydrophilic group with the hydrophobic group; and n is an integer of at least 1 and up to the number of functional groups present in $R^1$. Typically n is 1 to 3, often 1 to 2, and more often 1.

In one particular embodiment, the hydrophilic group is a carbohydrate or a derivative thereof. Exemplary hydrophilic groups of the invention include galactose, glucose, lactose, maltose, mannose, rhamnose, sophorose, arabinose, and 2-, 3-, and/or 5-deoxy derivatives thereof. The carbohydrate moiety can be a pyranose (or pyranoside, i.e., 6-membered ring) or a furanose (or furanoside, i.e., 5-memebered ring) form. In addition, the carbohydrate can be mono-, di- or polysaccharides.

Surfactants of the invention also include a hydrophobic group such as a lipid or a hydrocarbon moiety. Typically surfactants of the invention include a single or multiple hydrocarbon chains of varying lengths with different pendant functional groups. In particular, the hydrophobic moiety is often used to tune surfactant or emulsifying behavior of surfactants.

Some of the particular surfactants of the invention include a hydrophilic moiety of the formula:

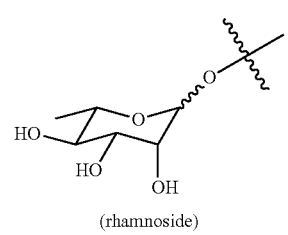

(rhamnoside)

1A

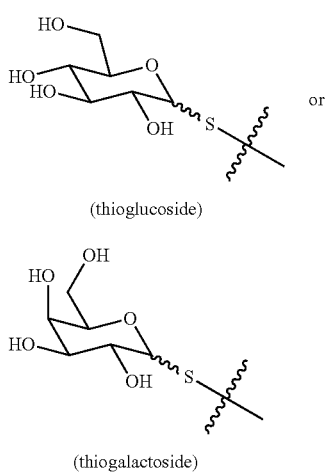

(thioglucoside)

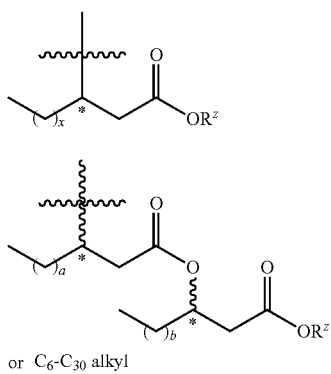

(thiogalactoside)

with the following hydrophobic groups:

[Structure 2A]

[Structure 2B]

or C$_6$-C$_{30}$ alkyl where R$^z$ is hydrogen, alkyl, benzyl, or other carboxylic acid protecting group; x is an integer from 6 to 14, in particular 6 or 10; a is an integer from 2 to 18, typically 2 to 16, in particular 2, 6, 10, 12 or 14; b is an integer from 2 to 18, typically 2 to 16, in particular 2, 4, 6, 8, 10, 12 or 14. Typically, alkyl group is C$_6$-C$_{22}$ alkyl, in particular alkyl group is C$_8$, C$_9$ or C$_{12}$ alkyl. The hydrophilic group is typically attached to the 1-, 2-, or the 3-position of the hydrophobic group; however, it should be appreciated that the scope of the invention is not limited to these positions of substitution. In one particular embodiment, the alkyl hydrophobic group is a linear chain alkyl group. It should also be appreciated that each chiral center of the hydrophobic group (e.g., each chiral carbon atom indicated by *) can be independently enantiomerically enriched (R)- or (S)-stereoisomer, or a racemic mixture.

Still further, combinations of the various hydrophilic groups and hydrophobic groups described herein form other specific embodiments of the invention. For example, in one particular embodiment the hydrophilic group is rhamnose and the hydrophobic group is 2A where x is 6, 10, 12 or 14; in another embodiment, the hydrophilic group is rhamnoside and the hydrophobic group is 2B where a is 2, 6, 10, 12 or 14 and b is 2, 4, 6, 8, 10, 12 or 14. Still in anther embodiment, the hydrophilic group is rhamnose and the hydrophobic group is C$_9$ or C$_{10}$ alkyl. Within this embodiment, in some instances C$_9$ or C$_{10}$ alkyl is a straight chain alkyl in which the 2-position is attached to rhamnose. In still another example, the hydrophilic group is glucose, galactose or dodecyl. Is should be appreciated that the functional group that links the hydrophilic group to the hydrophobic group is derived from the functional group that is present in the hydrophobic compound, e.g., the thiol group in moieties 2A and 2B are derived from the functional group of hydrophobic compound. Within this embodiment, in some instances the 1-position of dodecyl is attached to the hydrophilic group. In this manner, a variety of surfactants are embodied within the invention.

Synthesis

There are a variety of publications and patents providing many different chemical syntheses for glycolipids; however, many of these methods are specific to a single carbohydrate and single lipid; these procedures range from solid-phase to solution-phase techniques at low or high temperatures, the latter reactions being achieved by microwave or conventional heating. However, microwave-assisted reactions can be limited in scalability. Additionally, many chemical methodologies for glycolipids require multiple reaction steps in order to prepare glycosyl compounds for glycosylation with lipids. Furthermore, conventional glycosylation procedures can be expensive, dangerous, and some even require non-catalytic amount of a relatively expensive and/or toxic glycosylation promoters.

In contrast, methods of the invention can be used to produce a vast number of surfactants with a variety of carbohydrates as a hydrophilic group and a variety of hydrophobic groups including, but not limited to, lipids and hydrocarbons in a cost-effective and time-efficient manner. Because of the generality of this methodology, the synthesis and development of new species of surfactants, in particular glycolipid biosurfactants, can be achieved in order to not only compete in the markets for amphiphilic molecules, but improve these markets through the vast applicability of these glycolipids for multiple purposes. For instance, there are a variety of O- and S-linked glycolipids used in personal care products and cosmetics, and N-linked glycolipids have been shown to be excellent drug-delivery systems, such as the case with many glycopeptides.

One of the major advantages of methods of the invention is that surfactants are produced using a chemical procedure. Thus, unlike biological procedures for producing glycolipids, methods of the invention do not require extraction and purification from the bacteria. Moreover, unlike biological process-based glycolipid production, methods of the invention allow for production of single congeners that may be present in only small amounts in the congener mixture produced by bacteria. Therefore, the chemical synthesis is cost-effective, high yielding, scalable and requires less time to produce a variety of glycolipids compared to biological means. Additionally, a general synthetic method allows for the simple tailoring and production of novel glycolipids. These novel glycolipids can have different physical properties and amphiphilic characteristics depending on the hydrophilic moiety and/or the hydrophobic moiety used.

In some embodiments, methods of the invention include contacting a hydrophilic compound and a hydrophobic compound in the presence of a glycosylation promoter catalyst under conditions sufficient to produce the desired surfactant. In one particular embodiment, the hydrophilic compound is a carbohydrate moiety. Within this embodiment, in some instances the hydrophilic compound is a protected carbohydrate. Typically, the protecting group of the hydroxyl group of the carbohydrate is such that it can be displaced in the reaction to produce a relatively stable anion. For example, the pKa of the counter acid of the displaced protecting group in the glycosylation reaction is about 12 or less, typically 10 or less, often 8 or less, more often 7 or less and most often 6 or less. Exemplary counter acids of the displaced protecting group include, but are not limited to, organic acids (such as acetic acid, benzoic acid, trifluoroacetic acid, butyric acid, propionic acid, etc.), as well as other compounds whose counter acids are relatively strong. In one particular instance, one or more of the hydroxyl group of the carbohydrate is protected as acetic ester or benzoic ester. While one or more of the hydroxyl groups of the carbohydrate can have different protecting group(s), for simplicity and cost-effectiveness, typically all of the hydroxyl groups of the carbohydrate is protected with the same protecting group. Thus, in some instances, the carbohydrate is a peracetate or perbenzoylate carbohydrate. It should be appreciated, however, that the scope of the invention is not limited to hydroxyl groups of the carbohydrate having the same protecting group.

In general, the most challenging synthetic step of conventional glycolipid synthesis is the glycosylation step. This is due to the highly reactive characteristics of common carbohydrate donors and the typical use of moisture-sensitive promoters, which can cause low-yielding reactions, side-product formation and carbohydrate degradation.

Scheme 1 illustrates one particular reaction scheme of methods of the invention. As shown in Scheme 1, typical reaction condition includes a hydrophilic compound, a hydrophobic compound, and a glycosylation promoter. The glycosylation promoters of the invention are relatively weak Lewis acids and are used in a catalytic amount rather than in stoichiometric amount. Typically, the amount of glycosylation promoter used in methods of the invention is about 0.5 equivalent or less, typically 0.3 equiv. or less, often 0.25 equiv. or less, more often 0.2 equiv. or less, and most often 0.1 equiv. or less.

muth (III) trifluoromethanesulfonate, bismuth (III) bromide, bismuth (III) chloride, etc.), scandium(III) compounds (e.g., scandium (III) trifluoromethanesulfonate, etc.), boron compounds (e.g., boron trifluoride diethyl etherate), and indium (III) compounds (e.g., indium (III) bromide and indium (III) chloride). Unlike conventional glycosylation reactions, methods of the invention do not require stoichiometric or even excess amounts of often expensive, unstable and/or exotic glycosylation promoters. Moreover, the reaction times in methods of the invention are typically shorter than conventional glycosylation reactions.

Typically, the glycosylation reaction of the invention is carried out in a solvent. Suitable solvents include, but are not limited to, acetonitrile, benzene, dichloromethane, chloroform, carbon tetrachloride, dibromomethane, 1,2-dichloroethane, toluene, nitrobenzene, benzonitrile, tetrahydrofuran, diethyl ether, dibutylether, diisopropylether, dimethylformamide, and a combination of two or more thereof.

Hydrophobic compounds can include primary and secondary alcohols, amines, or thiols having at least six carbon chain length. Exemplary hydrophilic compounds include carbohydrates such as rhamnose, glucose, lactose, galactose, and mannose. Typically the carbohydrate used is protected as peracetates or perbenzoylates. However, it should be appreciated that, as discussed above, the scope of the invention is not limited to these particular protecting groups.

The Table below shows the yield of the glycosylation between rhamnose peracetate and various alkyl alcohols (1-decanol, 2-decanol and benzyl 3-hydroxydecanoate) in the presence of glycosylation promoter $Bi(OTf)_3$ or $InBr_3$. All reactions were conducted at the same temperature, concentration, and reagent equivalencies for comparison of the glycosylation promoter efficiencies.

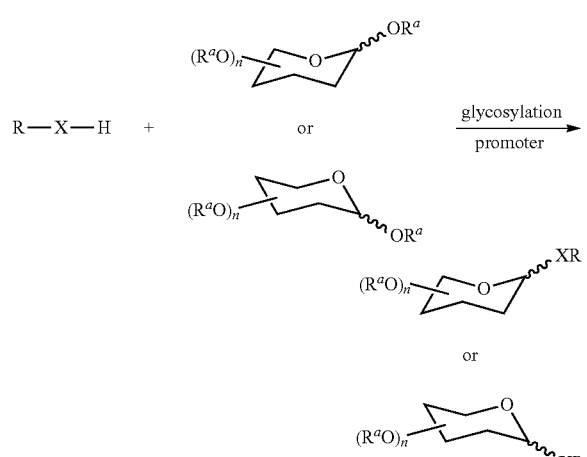

| R—OH | Glycosylation Promoter | Yield (%) |
|---|---|---|
| 1-decanol | $Bi(OTf)_3$ | 91 |
|  | $InBr_3$ | 89 |
| 2-decanol | $Bi(OTf)_3$ | 89 |
|  | $InBr_3$ | 83 |
| Benzyl 3-hydroxydecanoate | $Bi(OTf)_3$ | 60 |
|  | $InBr_3$ | 38 |

The result of glycosylation reactions using perbenzoylate rhamnose as the hydrophilic moiety is shown below. As can be seen, in general, the yield of the glycosylated products using a bismuth (III) compound as a glycosylation promoter is higher compared to reactions where an indium (III) compound is used as a glycosylation promoter. Moreover, generally bismuth (III) compounds are less hygroscopic and regarded as nontoxic compared to indium (III) compounds. Thus, in some embodiments, the glycosylation promoter is a bismuth (III) compound. Within these embodiments, in As can be seen in Scheme 1, the anomeric acetate or benzoylate is displaced in the reaction and is substituted with the hydrophobic moiety to produce the surfactant. Exemplary glycosylation promoters for this purpose include, but are not limited to, bismuth (III) compounds (e.g., bissome instances the glycosylation promoter comprises bismuth trifluoromethanesulfonate, bismuth halide, or a mixture thereof. Results of glycosylation using perbenzoylated rhamnose as the hydrophilic compound.

| R—OH | Glycosylation Promoter | Yield (%) |
|---|---|---|
| 1-decanol | Bi(OTfl)$_3$ | 77 |
|  | InBr$_3$ | 33 |
| 2-decanol | Bi(OTfl)$_3$ | 46 |
|  | InBr$_3$ | 24 |
| Benzyl 3-hydroxydecanoate | Bi(OTfl)$_3$ | 33 |
|  | InBr$_3$ | No Reaction |

The table below shows the yield of glycosylation reactions using BF$_3$.Et$_2$O, Sc(OTfl)$_3$, and InBr$_3$ as the glycosylation promoter. As can be seen, the glycosylation reaction required at least a stoichiometric amount (i.e., 1 equivalent or more) of BF$_3$.Et$_2$O and Sc(OTfl)$_3$ glycosylation promoters. In contrast, only a catalytic amount of InBr$_3$ glycosylation promoter is needed to provide a sufficiently high yield of the desired glycosylation product.

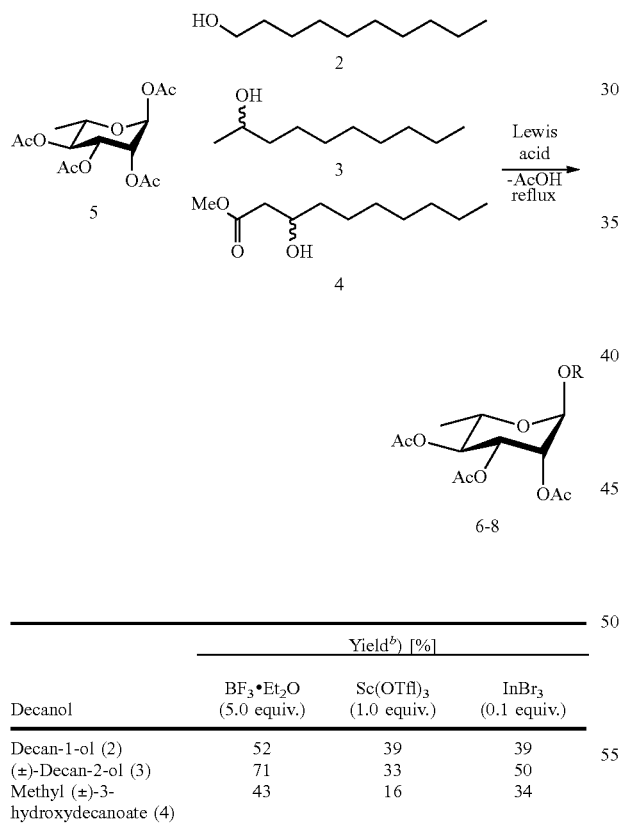

|  | Yield[b] [%] | | |
|---|---|---|---|
| Decanol | BF$_3$•Et$_2$O (5.0 equiv.) | Sc(OTfl)$_3$ (1.0 equiv.) | InBr$_3$ (0.1 equiv.) |
| Decan-1-ol (2) | 52 | 39 | 39 |
| (±)-Decan-2-ol (3) | 71 | 33 | 50 |
| Methyl (±)-3-hydroxydecanoate (4) | 43 | 16 | 34 |

[a] Conditions: 2.2 equiv. of L-rhamnose peracetate 5 and 1 equiv. of decanol 2, 3, or 4 in ClCH$_2$Cl$_2$Cl at 60° in a sealed tube.
[b] Yield of 6 (from 2), 7 (from 3), and 8 (from 4).

A wide range of reaction temperatures can be used in methods of the invention. Typically, the reaction temperature used for glycosylation depends on a variety of factors including the glycosylation promoter, hydrophilic compound, hydrophobic compound, solvent, as well as the concentrations of each reagent used. Typically, glycosylation is carried out at the reaction temperature of 30° C. or higher, often 40° C. or higher, more often 50° C. or higher, and most often at the boiling point of solvent.

The hydroxy protecting groups can be removed using a standard deprotection reaction known to one skilled in the art. See, for example, T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. In this manner, a wide variety of carbohydrate-based surfactants are produced using the methods of the invention. Representative compounds that are produced using the methods of the invention include, but are not limited to, the following compounds:

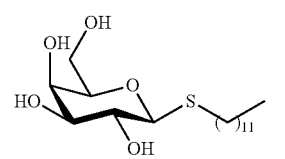

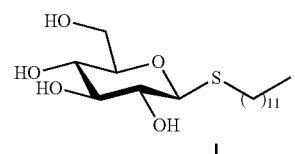

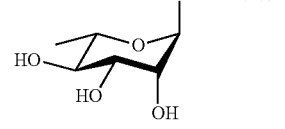

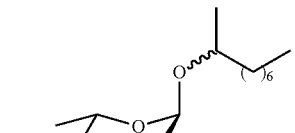

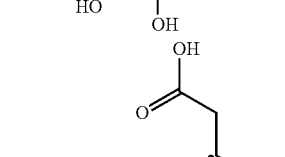

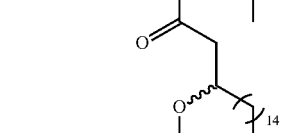

-continued
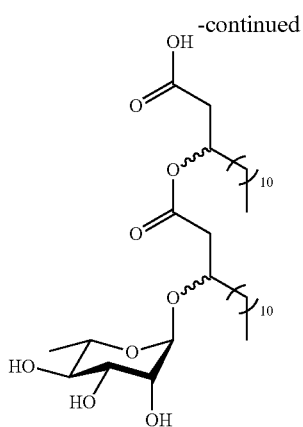
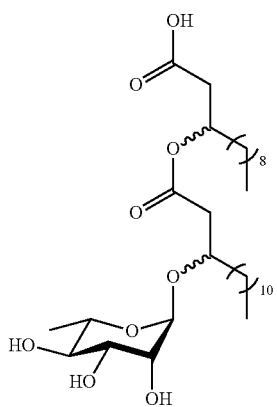
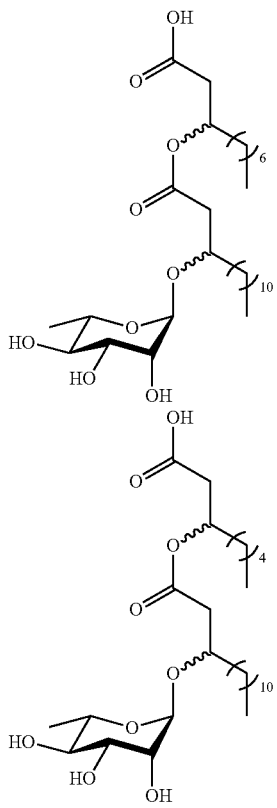
-continued
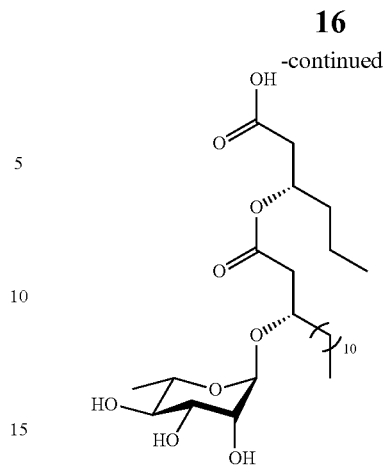
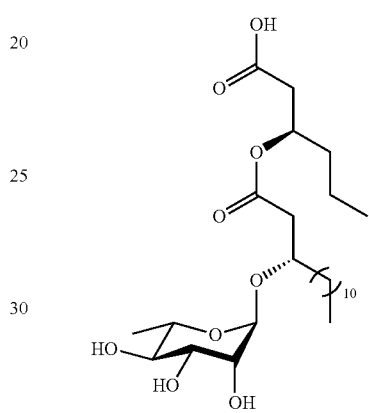
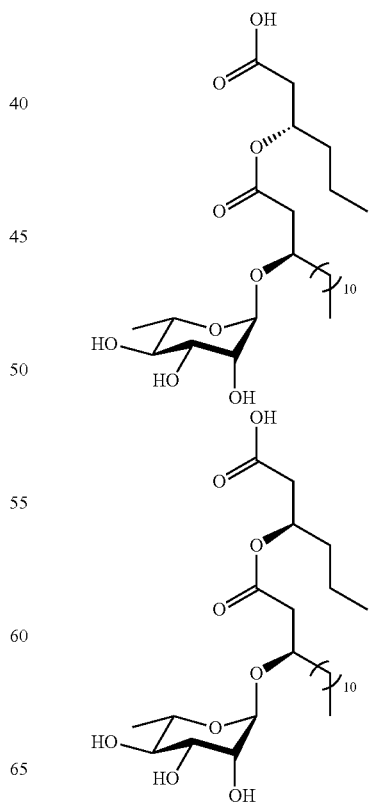

17
-continued
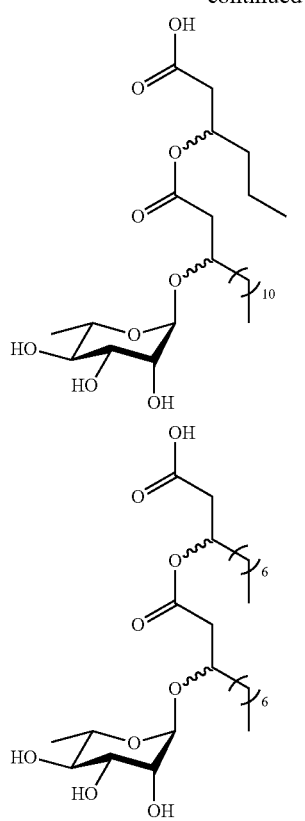
18
-continued
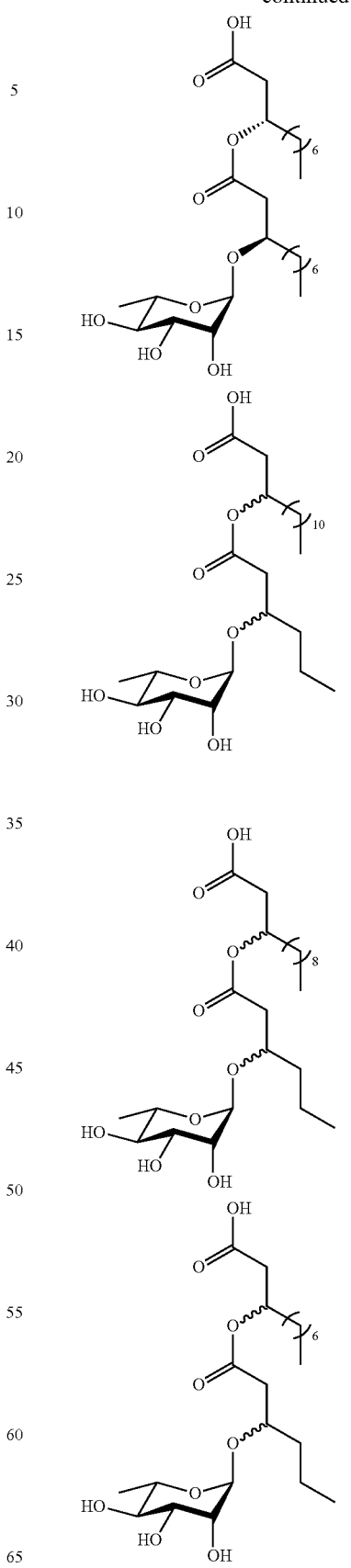

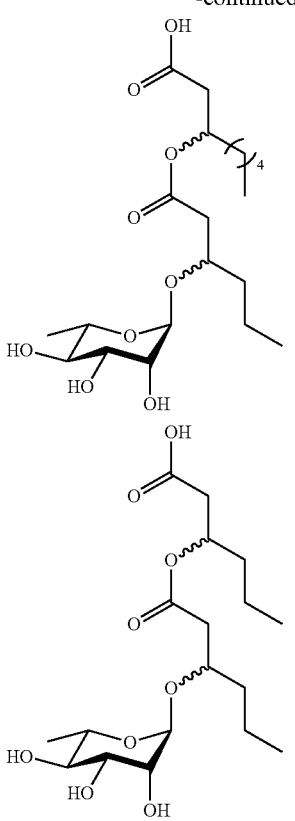

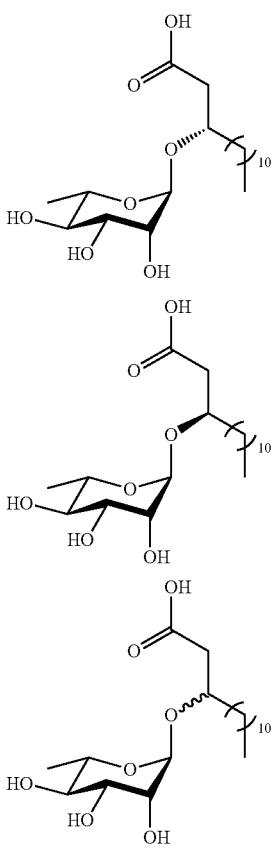

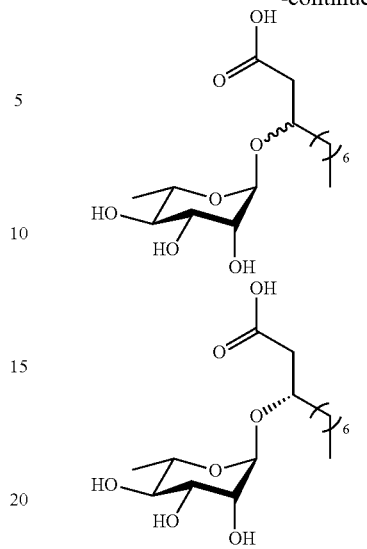

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

All glassware was flame-dried prior to reactions, and all reactions were done under Ar. Microwave: 900 W Emerson MW8992SB microwave oven, purchased from a Target department store. Flash chromatography (FC): silica gel 60 ($SiO_2$, 200-400 mesh; Geduran No. EM-11567-1); Horizon HPFC system (Biotage, Inc.). HPLC: Varian-Prostar HPLC system, with a Prostar-330 photodiode array detector and a Phenomenex-Jupiter (250 mm×21.2 mm, 15 µm) $C_{18}$ semi-prep. column. M.p.: uncorrected. $^1H$ and $^{13}C$ NMR Spectra: Bruker-DRX-400 (400 MHz), -DRX-500 (500 MHz), and -DRX-600 (600 MHz) spectrometers; in $CDCl_3$, $(D_6)$ DMSO, or $CD_3OD$; δ in ppm rel. to $Me_4Si$ as internal standard, J in Hz; all NMR spectra were analyzed and interpreted with the MestReNova software. ESI-MS: Thermo-Finnigan LCQ Deca with pos. and neg. detection, $MeOH/H_2O$ 1:1 solvent system; in m/z (rel. %).

Decyl β-Lactoside. A mixture of potassium acetate (i.e., AcOK) (6.56 g, 66.8 mmol) and acetic anhydride (i.e., $Ac_2O$) (21 ml, 220 mmol) was heated under reflux, followed by slow addition of lactose (1.01 g, 2.79 mmol) to the boiling mixture. The mixture was stirred for 5 min and allowed to cool to r.t., where it was then diluted with $CH_2Cl_2$ and washed with ice-cold $H_2O$, 1% $NaHCO_3$, sat. $NaHCO_3$, and sat. NaCl soln. The org. layer was dried ($MgSO_4$) and concentrated to a colorless oil which was then dissolved in a minimal amount of $CH_2Cl_2$ and recrystallized by addition of $Et_2O$: β-lactose peracetate (58%). White, crystalline solid. M.p. 104-106° C.

The β-lactose peracetate (1.78 g, 2.62 mmol), decan-1-ol (0.50 ml, 2.62 mmol), and $InBr_3$ (0.093 g, 0.262 mmol) were added to a 50 ml triple-walled resealable vessel (internally threaded with a Teflon plug), dissolved in $ClCH_2CH_2Cl$ (3-4 ml), and irradiated in a 900 W Emerson-MW8992SB microwave oven (power level 6) for 2 min. The crude yellow oil was purified by FC (gradient AcOEt/hexanes 1:9→2:8→3:7→4:6): decyl β-lactoside peracetate (60%). White foam. M.p. 94-99° C. $^1$H-NMR (500 MHz, CDCl$_3$): 5.31 (d, J.3.2, 1 H); 5.16 (t, J.9.3, 1 H); 5.07 (dd, J.10.4, 7.9, 1 H); 4.92 (dd, J.10.4, 3.4, 1 H); 4.85 (dd, J.9.5, 8.0, 1 H); 4.49-4.38 (m, 3 H); 4.15-4.01 (m, 3 H); 3.87-3.72 (m, 3 H); 3.56 (ddd, J.9.8, 5.0, 1.9, 1 H); 3.41 (dt, J.9.6, 6.8, 1 H); 2.12 (s, J.2.9, 3 H); 2.09 (s, J.7.8, 3 H); 2.06-1.97 (m, 12 H); 1.93 (s, J.5.9, 3 H); 1.58-1.45 (m, 2 H); 1.33-1.16 (m, 14 H); 0.85 (t, J.6.9, 3 H). $^{13}$C-NMR (125 MHz, CDCl$_3$): 170.2; 170.2; 170.0; 169.9; 169.6; 169.4; 168.9; 101.0; 100.6; 76.3; 72.9; 72.6; 71.8; 71.0; 70.7; 70.2; 69.2; 66.7; 62.1; 60.8; 31.9; 29.6; 29.5; 29.4; 29.3; 29.3; 25.8; 22.7; 20.8; 20.8; 20.7; 20.6; 20.5; 14.1. ESI-MS (pos.): 815.1 (17, [M+K]$^+$), 799.2 (99, [M+Na]$^+$), 794.1 (53, [M+NH$_4$]$^+$).

The decyl β-lactoside peracetate (2.93 g, 3.77 mmol) was dissolved in dry MeOH (30 ml) under Ar, and a 25% (wt./v) MeONa/MeOH soln. (0.5 ml) was added dropwise until the soln. reached pH 9-10. The mixture was stirred for 24 h (TLC monitoring) and then neutralized by Dowex 50WX8-100 ion exchange resin. The mixture was filtered and the filtrate concentrated: decyl β-lactoside (72%). White solid. M.p. 140-160° C. (dec.). $^1$H-NMR (500 MHz, (D$_6$)DMSO): 6.04 (s, 1 H); 5.84-5.31 (m, 4 H); 5.17 (dd, J.19.1, 7.5, 2 H); 4.73 (dt, J.6.6, 5.8, 2 H); 4.67-4.14 (m, 19 H); 3.99 (t, J.8.2, 1 H); 3.50 (dt, J. 3.6, 1.8, 1 H); 2.37-2.13 (m, 14 H); 1.85 (t, J.6.9, 3 H). $^{13}$C-NMR (125 MHz, (D$_6$)DMSO): 103.8; 102.5; 80.8; 75.5; 75.0; 74.8; 73.2; 73.1; 70.6; 68.7; 68.1; 60.6; 60.4; 31.3; 29.3; 29.0; 29.0; 28.9; 28.7; 25.5; 22.1; 14.0. ESI-MS (pos.): 987.0 (100, [2 M+Na]$^+$), 964.9 (13, [2 M+H]$^+$), 505.4 (12, [M+Na]$^+$), 482.9 (10, [M+H]$^+$).

Microwave Procedure for Rhamnosides 6-8. Rhamnose peracetate 5 (1.2 equiv.), alcohol (1 equiv.), and Sc(OTf)$_3$ (1 equiv.), InBr$_3$ (0.1 equiv.), or BF$_3$.Et$_2$O (5 equiv.) were dissolved in dry ClCH$_2$CH$_2$Cl (1.5 ml) in a flame-dried triple-walled resealable vessel (internally threaded with a Teflon plug), and the vessel was microwave-irradiated (900 W Emerson MW8992SB) for 2 min on power level 6. The slightly yellow mixture was neutralized with sat. NaHCO$_3$ soln., the org. layer washed with H$_2$O, dried (MgSO$_4$), and concentrated, and the obtained oil purified by FC (20% AcOEt/hexanes).

Decyl 6-Dexoy-α-L-mannopyranoside Triacetate (6): Colorless oil. R$_f$ (30% AcOEt/hexanes) 0.64. $^1$H-NMR (500 MHz, CDCl$_3$): 5.28 (dd, J.10.1, 3.5, 1 H); 5.20 (dd, J.3.5, 1.7, 1 H); 5.03 (t, J.9.9, 1 H); 4.68 (d, J.1.5, 1 H); 3.84 (dq, J.9.9, 6.3, 1 H); 3.63 (dt, J.9.5, 6.8, 1 H); 3.39 (dt, J.9.6, 6.6, 1 H); 2.12 (s, 3 H); 2.02 (s, 3 H); 1.96 (s, 3 H); 1.59-1.53 (m, 2 H); 1.35-1.21 (m, 14 H); 1.19 (d, J.6.3, 3 H); 0.86 (t, J.6.9, 3 H). $^{13}$C-NMR (125 MHz, CDCl$_3$): 170.2; 170.0; 169.9; 97.4; 71.3; 70.0; 69.2; 68.2; 66.2; 31.9; 29.6; 29.5; 29.4; 29.3; 29.3; 26.1; 22.7; 20.9; 20.8; 20.7; 17.4; 14.1.

(1R)- and (1S)-1-Methylnonyl 6-Deoxy-α-L-mannopyranoside Triacetate (7; diastereoisomer mixture 1:1): Colorless oil. R$_f$ (30% AcOEt/hexanes) 0.68. $^1$H-NMR (500 MHz, CDCl$_3$): 5.28 (dd, J.10.1, 3.5, 1 H); 5.25 (dd, J.10.1, 3.5, 1 H); 5.15-5.11 (m, 2 H); 5.02 (t, J.9.9, 1 H); 5.01 (t, J.10.0, 1 H); 4.79 (d, J.1.7, 1 H); 4.77 (d, J.1.7, 1 H); 3.92 (dq, J.9.8, 6.3, 1 H); 3.89 (dq, J.9.8, 6.3, 1 H); 3.70 (dt, J.11.8, 6.0, 1 H); 3.64 (dt, J.12.4, 6.1, 1 H); 2.11 (s, 6 H); 2.01 (s, 3 H); 2.01 (s, 3 H); 1.95 (s, 6H); 1.60-1.44 (m, 2 H); 1.44-1.30 (m, 2H); 1.26 (dd, J.26.5, 8.0, 24 H); 1.16 (d, J.6.3, 9 H); 1.08 (d, J.6.1, 3 H); 0.84 (t, J.6.9, 3 H); 0.84 (t, J.7.0, 3 H). $^{13}$C-NMR (125 MHz, CDCl$_3$): 170.2; 170.1; 170.0; 169.9; 169.9; 97.0; 94.7; 75.8; 73.1; 71.4; 71.2; 70.6; 70.4; 69.2; 69.2; 66.4; 66.2; 36.9; 36.2; 31.8; 31.8; 29.6; 29.5; 29.5; 29.5; 29.2; 29.2; 25.6; 25.3; 22.6; 21.1; 20.9; 20.8; 20.7; 18.9; 17.3; 17.3; 14.1.

Methyl (3R)- and (3S)-3-[(2,3,4-Tri-O-acetyl-6-deoxy-α-L-mannopyranosyl)oxy]decanoate (8; diastereoisomer mixture 1:1): Colorless oil. R$_f$ (pair of diastereoisomers) 0.45 and 0.40. $^1$H-NMR (500 MHz, CDCl$_3$): 5.21 (d, J.3.4, 1 H); 5.19 (d, J.3.4, 1 H); 5.11 (dd, J.3.4, 1.8, 1 H); 5.07 (dd, J. 3.4, 1.8, 1 H); 5.01 (t, J.9.9, 1 H); 4.99 (t, J.10.0, 1 H); 4.83 (d, J.1.5, 1 H); 4.80 (d, J.1.5, 1 H); 4.10-3.97 (m, 2 H); 3.94-3.82 (m, 2 H); 3.66 (s, 3 H); 3.65 (s, 3 H); 2.54 (dd, J.15.3, 8.1, 1 H); 2.50 (dd, J.15.5, 7.5, 1 H); 2.44 (dd, J.15.4, 6.4, 1 H); 2.43 (dd, J.15.4, 6.9, 1 H); 2.10 (d, J.2.8, 6 H); 2.00 (d, J.3.0, 6 H); 1.93 (d, J.1.9, 6 H); 1.63-1.40 (m, 4 H); 1.36-1.17 (m, 16 H); 1.16 (d, J.6.3, 1 H); 1.15 (d, J.6.2, 1 H); 0.83 (td, J.6.9, 3.5, 6 H). $^{13}$C-NMR (125 MHz, CDCl$_3$): 171.7; 171.6; 170.1; 170.0; 169.9; 169.9; 169.9; 97.5; 95.9; 76.3; 74.9; 71.1; 70.3; 70.2; 69.1; 69.0; 66.7; 66.6; 51.7; 51.6; 39.9; 39.3; 35.0; 33.3; 31.7; 31.7; 29.4; 29.4; 29.1; 29.1; 25.1; 24.7; 22.6; 22.6; 20.9; 20.9; 20.8; 20.7; 17.2; 17.2; 14.0.

Conventional Reflux Procedure for Rhamnosides. To a soln. of rhamnose peracetate 5 (2.2 equiv.) in dry MeCN, the alcohol (1 equiv.) (2, 3 or benzyl ester of 4) and either Bi(OTfl)$_3$ (0.10 equiv.) or InBr$_3$ (0.10 equiv.) were added. The mixture was refluxed under a Liebig condenser for 2.5 h and then allowed to cool to r.t. For Bi(OTfl)$_3$, the yellow-brown mixture was diluted with CH$_2$Cl$_2$, Celite was added, the mixture filtered, and the filtrate concentrated to a yellow-brown syrup. For InBr$_3$, the yellow mixture was diluted with CH$_2$Cl$_2$ and neutralized with sat. NaHCO$_3$ soln., and the org. layer washed with H$_2$O, dried (MgSO$_4$), and concentrated. Purification was achieved by FC (gradient hexanes/AcOEt 0→20%). Yields of 89%, 83%, 38% for InBr$_3$ and 91%, 89% and 60% for Bi(OTfl)$_3$ for alcohols 2, 3 and benzyl ester of 4, respectively.

Phenylmethyl (3R)- and (3S)-3-[(2,3,4-Tri-O-acetyl-6-deoxy-α-L-mannopyranosyl)oxy]decanoate (diastereoisomer mixture 45:55): Colorless oil. R$_f$ (30% AcOEt/hexanes) 0.55. $^1$H-NMR (500 MHz, CDCl$_3$): 7.36-7.27 (m, 10 H); 5.23 (ddd, J.10.1, 3.4, 1.0, 2 H); 5.14 (dt, J.4.4, 2.2, 1 H); 5.13-5.10 (m, 5 H); 5.02 (td, J.10.0, 5.9, 2 H); 4.87 (d, J.1.6, 1 H); 4.83 (d, J.1.6, 1 H); 4.14-4.02 (m, 2 H); 3.95-3.86 (m, 2 H); 2.66-2.46 (m, 4 H); 2.12 (d, J.5.9, 6 H); 2.04-1.99 (m, 6 H); 1.96 (d, J.1.5, 6 H); 1.63-1.43 (m, 4 H); 1.37-1.19 (m, 23 H); 1.18 (d, J.6.3, 3 H); 1.15 (d, J.6.3, 3 H); 0.85 (td, J.6.9, 3.7, 6 H). $^{13}$C-NMR (125 MHz, CDCl$_3$): 171.1; 170.9; 170.1; 170.0; 169.9; 135.7; 135.7; 128.5; 128.5; 128.4; 128.2; 128.2; 97.4; 96.2; 76.1; 75.1; 71.1; 70.3; 70.2; 69.1; 69.1; 66.7; 66.7; 66.5; 66.4; 40.2; 39.5; 35.0; 33.4; 31.7; 29.5; 29.4; 29.1; 29.1; 25.1; 24.7; 22.6; 22.6; 20.9; 20.8; 20.7; 17.3; 14.1.

(3R)- and (3S)-3-[(2,3,4-Tri-O-acetyl-6-deoxy-α-L-mannopyranosyl)oxy]decanoic Acid (diastereomeric mixture; (R)-11 and (S)-11, resp.). To a soln. of 10 (8.57 g, 15.6 mmol) in dry THF (100 ml) at r.t., a small amount of 10% (wt.) Pd/C was added under Ar. By means of a balloon, the flask was filled with H$_2$ gas (1 atm) and the mixture stirred vigorously at r.t. for 24 h. Then the mixture was purged with Ar, diluted with CH$_2$Cl$_2$, and filtered through Celite, the filtrate was concentrated, and the resulting oil was purified by FC (Et$_2$O/hexanes 1:1 with 1% AcOH): (R)-11 (38%) and (S)-11 (33%).

Data of (R)-11: Colorless oil. [a]$_D$=−30.6 (c=1.0, CHCl$_3$). R$_f$ (Et$_2$O/hexanes 1:1 with 1% (v/v) AcOH) 0.26. $^1$H-NMR (400 MHz, CDCl$_3$): 5.24 (dd, J.10.1, 3.5, 1 H); 5.12 (dd, J.3.4, 1.8, 1 H); 5.03 (t, J.9.9, 1 H); 4.89 (d, J.1.8, 1 H); 4.04

(dq, J.11.7, 5.9, 1 H); 3.93 (dq, J.9.8, 6.3, 1 H); 2.57 (dd, J.15.8, 7.5, 1 H); 2.49 (dd, J.15.8, 5.3, 1 H); 2.11 (s, 3 H); 2.03 (s, 3H); 1.96 (s, 3 H); 1.65-1.50 (m, 2 H); 1.32-1.22 (m, 10 H); 1.18 (d, J.6.3, 3 H); 0.89-0.84 (m, 3H). $_{13}$C-NMR (100 MHz, CDCl$_3$): 176.2; 170.2; 170.1; 170.1; 97.5; 76.2; 71.1; 70.3; 69.1; 66.8; 39.3; 35.0; 31.7; 29.4; 29.1; 25.1; 22.6; 20.9; 20.8; 20.7; 20.7; 17.3; 14.0.

Data of (S)-11: Clear oil. [a]$_D$=−47.9 (c=1.0, CHCl$_3$); R$_f$ (Et$_2$O/hexanes 1:1 with 1% (v/v) AcOH) 0.38. $^1$H-NMR (400 MHz, CDCl$_3$): 5.23 (dd, J.10.1, 3.4, 1 H); 5.14 (dd, J.3.4, 1.8, 1 H); 5.02 (t, J.9.9, 1 H); 4.82 (d, J.1.7, 1 H); 4.07 (dq, J.7.5, 5.9, 1 H); 3.93 (dq, J.9.9, 6.3, 1 H); 2.63 (dd, J.15.9, 7.6, 1 H); 2.52 (dd, J.15.9, 4.8, 1 H); 2.12 (s, 3 H); 2.02 (s, 3 H); 1.96 (s, 3H); 1.52 (ddd, J.23.0, 14.2, 5.3, 2 H); 1.32-1.21 (m, 10 H); 1.15 (d, J.6.3, 3 H); 0.87-0.82 (m, 3H). $^{13}$C-NMR (100 MHz, CDCl$_3$):176.7; 170.2; 170.1; 170.0; 96.4; 75.1; 71.1; 70.3; 69.1; 66.8; 39.9; 33.6; 31.7; 29.5; 29.1; 24.8; 22.6; 20.9; 20.8; 20.7; 17.2; 14.0.

(3R)- and (3S)-3-(6-Deoxy-α-L-mannopyranosyloxy)decanoic Acid (diastereomeric mixture; (R)-1 and (S)-1, resp.). To a soln. of (R)-11 (5.77g, 12.5 mmol) in dry MeOH (50 ml) at r.t., MeONa was added while stirring to achieve a pH 9-10 (monitoring by a drop of the mixture onto a moistened pH-indicator strip). The mixture was stirred at r.t. for 3.5 h and then quenched with Dowex H resin. The resin was removed by filtration and the filtrate concentrated to an oil. No further purification was required. However, redissolving of the product in a minimal amount of hexanes, followed by filtration, was occasionally required to remove residual Na salts: (R)-1 (99%). Colorless oil. [a]$_D$=−34.8 (c=1.0, MeOH). R$_f$ (10% MeOH/CH$_2$Cl$_2$ with 1% (v/v) AcOH) 0.20. $^1$H-NMR (400 MHz, CD$_3$OD): 4.75 (d, J.1.7, 1 H); 3.96-3.89 (m, 1 H); 3.65 (dd, J.3.4, 1.7, 1 H); 3.61-3.53 (m, 1 H); 3.51 (dd, J.9.5, 3.4, 1 H); 3.29-3.24 (m, 1 H); 2.34 (qd, J.15.0, 6.4, 2 H); 1.54-1.43 (m, 2 H); 1.26-1.17 (m, 10 H); 1.14 (d, J.6.3, 3 H); 0.80 (dd, J.7.9, 6.0, 3 H). $^{13}$C-NMR (100 MHz, CD$_3$OD): 176.2; 101.6; 76.9; 73.9; 72.7; 72.4; 70.2; 41.2; 36.4; 33.0; 30.7; 30.3; 26.3; 23.7; 17.9; 14.4. ESI-MS (neg.): 334.1 (12, M$_-$), 333.1 (99, [M−H]$^-$).

Glycolipid (S)-1 was obtained in the same fashion: Yield 99%. Colorless oil. [a]$_D$=−47.0 (c=1.0, MeOH). R$_f$ (10% MeOH/CH$_2$Cl$_2$ with 1% (v/v) AcOH) 0.25. $^1$H-NMR (400 MHz, CD$_3$OD): 4.66 (d, J. 1.7, 1 H); 3.93 (dq, J.7.5, 5.7, 1 H); 3.62 (dd, J.3.4, 1.7, 1 H); 3.58-3.45 (m, 2 H); 3.20 (t, J.9.5, 1 H); 2.33 (ddd, J.20.4, 14.8, 6.6, 2 H); 1.42 (dt, J.9.1, 6.2, 2 H); 1.21-1.13 (m, 10 H); 1.09 (d, J.6.2, 3 H); 0.77-0.73 (m, 3 H). $^{13}$C-NMR (100 MHz, CD$_3$OD): 176.5; 100.3; 75.9; 74.0; 72.7; 72.3; 70.1; 42.2; 34.5; 33.0; 30.7; 30.3; 25.9; 23.7; 17.9; 14.4. ESI-MS (neg.): 334.1 (12, M$_-$), 333.1 (99, [M−H]$^-$).

Synthesis of peracetylated C$_{10}$ rhamnosides via microwave-assisted glycosylation. In a flame-dried microwave bomb, rhamnose peracetate and methyl 3-hydroxydecanoate were dissolved in ClCH$_2$CH$_2$Cl. The glycosylation promoter was added and the vessel was microwave-irradiated for 1-3 minutes. The slightly yellow reaction mixture was neutralized using saturated NaHCO$_3$ and the layers were separated. The organic layers were washed with H$_2$O and dried over MgSO$_4$, filtered, and concentrated via rotary evaporation. The crude product was purified by column chromatography to give the products as colorless syrups. The yield of glycosylated products were 16%, 34% and 33% for Sc(OTfl)$_3$, InBr$_3$ and BF$_3$.OEt$_2$ glycosylation promoters, respectively.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for producing a carbohydrate-based surfactant, said method consisting essentially of contacting a carbohydrate comprising a protecting group with a hydrophobic compound in the presence of a catalytic amount of a glycosylation promoter under conditions sufficient to form a covalent bond between said carbohydrate and said hydrophobic compound to produce a carbohydrate-based surfactant, wherein said hydrophobic compound comprises a functional group selected from the group consisting of an amine group, a hydroxyl group and a thiol group, and wherein the functional group of said hydrophobic compound covalently links said hydrophobic compound to said carbohydrate and wherein said glycosylation promoter is selected from the group consisting of bismuth (III) compound, a scandium (III) compound, an indium (III) compound and a mixture thereof.

2. The method of claim 1, wherein said glycosylation promoter comprises a bismuth (III) compound.

3. The method of claim 2, wherein said bismuth (III) compound comprises bismuth trifluoromethanesulfonate, bismuth halide, or a mixture thereof.

4. The method claim 1, wherein the amount of glycosylation promoter used in the reaction is about 0.25 equivalent or less.

5. The method of claim 1, wherein said hydrophobic compound is a hydrocarbon compound of the formula R$^x$—X, wherein R$^x$ is a hydrocarbon and X is —OH, —NH$_2$, or —SH.

6. The method of claim 5, wherein R$^x$ is a C$_6$-C$_{30}$ hydrocarbon.

7. The method of claim 6, wherein R$^x$ is a C$_6$-C$_{18}$ hydrocarbon.

8. The method of claim 1 further comprising a step of removing said protecting group to produce said carbohydrate-based surfactant.

9. The method of claim 1, wherein said protecting group is a hydroxyl protecting group.

10. The method of claim 9, wherein said hydroxyl protecting group comprises an ester.

11. The method of claim 9, wherein said hydroxyl protecting group comprises acetate, benzoylate or a combination thereof.

* * * * *